(12) United States Patent
Mahajan et al.

(10) Patent No.: US 12,361,495 B2
(45) Date of Patent: Jul. 15, 2025

(54) DISTRIBUTED COMPUTING SYSTEM FOR BENEFITS PROCESSING USING PATIENT-CENTRIC PROFILING AND MACHINE LEARNING

(71) Applicant: Cambalt Solutions, Inc., Boston, MA (US)

(72) Inventors: Satyender Mahajan, Newton, MA (US); Ramakrishna R. Sudireddy, Andover, MA (US)

(73) Assignee: Cambalt Solutions, Inc., Boston, MA (US)

( * ) Notice: Subject to any disclaimer, the term of this patent is extended or adjusted under 35 U.S.C. 154(b) by 632 days.

(21) Appl. No.: 17/175,618

(22) Filed: Feb. 13, 2021

(65) Prior Publication Data

US 2021/0166329 A1    Jun. 3, 2021

Related U.S. Application Data

(63) Continuation of application No. 16/450,559, filed on Jun. 24, 2019, now Pat. No. 10,922,758.

(Continued)

(51) Int. Cl.
*G06Q 40/08* (2012.01)
*G06N 20/00* (2019.01)
(Continued)

(52) U.S. Cl.
CPC ............. *G06Q 40/08* (2013.01); *G06N 20/00* (2019.01); *G06Q 10/10* (2013.01); *G16H 10/60* (2018.01)

(58) Field of Classification Search
CPC ........ G06Q 40/08; G06Q 10/10; G16H 10/60; G06N 20/00
(Continued)

(56) References Cited

U.S. PATENT DOCUMENTS 5,778,345 A * 7/1998 McCartney ............ G06Q 10/06
705/2
6,283,761 B1 * 9/2001 Joao ........................ G16H 40/67
128/923

(Continued)

*Primary Examiner* — Michael Tomaszewski
(74) *Attorney, Agent, or Firm* — David H. Judson

(57) ABSTRACT

A computing system enables individuals and organizations to self-insure a benefit, e.g., a dental plan benefit. The system leverages a patient-centric data construct that evolves in a multi-dimensional manner as a patient continuously interacts with the system, its providers, participating organizations, etc. Using the patient-centric information repositories about the various participants (and their interactions), the system applies machine learning to the data to create data models that, in turn, provide valuable insights, or to otherwise enable more-efficient settlement processing. For example, a model may be used to determine an optimal patient-dentist match (by looking at utilization best provider outcomes), or a dentist over-provision of certain services (indicated by provider codes, thereby possibly indicative of fraud). Using patient-centric data modeling, the system determines if, when and how an organization can reduce expenses (e.g., by switching to other providers) or otherwise provide better care for participating employees. The data model(s) preferably evolve continuously, and the system dynamically-provisions computing resources as the patient-centric profiles evolve.

7 Claims, 2 Drawing Sheets

Related U.S. Application Data

(60) Provisional application No. 62/689,191, filed on Jun. 24, 2018.

(51) Int. Cl.
   *G06Q 10/10* (2023.01)
   *G16H 10/60* (2018.01)

(58) Field of Classification Search
   USPC .......................................................... 705/2–3
   See application file for complete search history.

(56) References Cited

U.S. PATENT DOCUMENTS

| | | | | |
|---|---|---|---|---|
| 8,200,506 B2* | 6/2012 | Kil | ......................... | G16H 20/00 |
| | | | | 705/2 |
| 2003/0009355 A1* | 1/2003 | Gupta | ..................... | G06Q 10/10 |
| | | | | 705/2 |
| 2006/0089862 A1* | 4/2006 | Anandarao | ............. | G06Q 40/08 |
| | | | | 705/4 |
| 2007/0226005 A1* | 9/2007 | Smith | ..................... | G16H 70/20 |
| | | | | 707/999.001 |
| 2007/0299698 A1* | 12/2007 | Anandarao | ............ | G06Q 40/08 |
| | | | | 705/4 |
| 2010/0312581 A1* | 12/2010 | Wachtell | ................. | G16H 40/20 |
| | | | | 707/812 |
| 2012/0303379 A1* | 11/2012 | Lash | ....................... | G06Q 40/00 |
| | | | | 705/2 |
| 2013/0197942 A1* | 8/2013 | Chiu | ...................... | G16H 40/67 |
| | | | | 705/3 |
| 2013/0339969 A1* | 12/2013 | Koski | .................... | G06Q 10/10 |
| | | | | 718/103 |
| 2014/0189702 A1* | 7/2014 | Yan | ........................ | G06F 9/5027 |
| | | | | 718/104 |
| 2015/0046292 A1* | 2/2015 | Zamer | ................ | G06Q 30/0629 |
| | | | | 705/26.64 |
| 2020/0294640 A1* | 9/2020 | Ginsburg | ............... | G16H 40/20 |

* cited by examiner

DISTRIBUTED COMPUTING SYSTEM FOR BENEFITS PROCESSING USING PATIENT-CENTRIC PROFILING AND MACHINE LEARNING

BACKGROUND

Technical Field

This application relates generally to data management in a distributed network.

Brief Description of the Related Art

When employers develop dental plans for their employees, they expect the dollars associated with those plans to go to dental care. This is not the case, however. According to studies done by the California Dental Association, nearly 40% of dental plan dollars are lost because of inefficiency. Additionally, one-third of adults with private dental plans do not go to the dentist even once per year, according to the American Dental Association. The result is employer dollars being paid into insurance companies, but not being paid back out for patient care. States across the country, including Massachusetts, have filed legislation to establish Minimum Loss Ratios (MLRs) for insurance companies to protect consumers, but nearly all of these bills do not include dental care.

Dental insurance is not actually insurance. Unlike health, car, home, and life insurance, where people pay into a risk pool to cover those that suffer unfortunate accidents or illnesses, dental does not have a risk pool. Dental insurance is actually benefit dollars that employers allocate for dental care; if there is an unfortunate emergency, often health (not dental) insurance covers it, or in many cases the emergency is not covered by either dental or medical insurance and has to be paid out-of-pocket.

One of the many problems associated with dental benefits is that the underlying technical systems and players are fragmented. In the usual case, a patient that wishes to receive dental services calls a dentist office to schedule an appointment. The dentist inputs an appointment into the Office practice management system. The patient goes to the provider and completes his or her appointment. Depending on the payer, the payment collection works differently. In the event the patient is paying out-of-pocket, with no insurance, payment is collected directly from the patient. In the event an employer is the payer, via an insurance company, the claim is sent via a clearinghouse to the insurance company for processing. The insurance company will then process the claim. Sometimes this is done automatically with payment being initiated almost immediately. In many cases, however, many claims require manual review and adjustment. Payment is then received by the provider from the insurance company after claims approval. Any remaining balance is then forwarded to the patient in a paper bill.

The current dental benefits market is highly inefficient and builds a black box around patient care. Insurance companies raise premiums on employers each year, and dentists and their staff are forced to chase claims.

There remains a need to address these and related problems associated with existing benefits plans and supporting computing networks.

BRIEF SUMMARY

This disclosure provides for a computing system and software platform that enables payers (individuals and corporations) to self-insure a benefit, e.g., a dental plan benefit. More generally, the computing platform provides a benefits management computing solution that enables individuals and companies to self-insure a benefit tied to certain providers. In one aspect, dental benefits are being managed by the computing platform, although this is not a limitation. Other applications include medical, vision, lab testing, veterinary and others. To create an optimal benefits management platform, the subject matter herein provides for an end-to-end computing solution that connects members, providers, and payers seamlessly while abstracting away the complexities of managing member information, service information, invoices, and payment transaction.

To this end, preferably, the computing platform of this disclosure leverages a data construct, which in the context of a dental benefit is sometimes referred to herein as a dental "patient profile." Unlike a provider's traditional service records that are simply static and just include a service treatment history for just the specific provider, the patient profile here is a patient-centric data construct that evolves in a multi-dimensional manner as a patient continuously interacts with the system, its providers, participating organization (employers), etc. The data structure preferably supports (or can reference) all of the information normally found in traditional service records, but it is also structured to include n-dimensions of additional data, including without limitation: benefits history, location information, provider history, employment history, personally-identifiable information, and more information, preferably according to an extensible data model. By establishing and maintaining this patient-centric repository of all available information about the various participants (and their interactions), the system then applies machine learning to the data to provide valuable insights, or to otherwise enable more-efficient processing of settlement(s).

For example, in one embodiment, an organization (a participating employer who uses the system) identifies a particular plan (e.g., a dental reimbursement plan) that is desires for its patient population. As employees use the system, the individual patient profile(s) evolve to include the data representing these patient-provider interactions. As these interactions continue, machine learning is applied against the data to generate an employer-specific model of patient utilization. A model may be applied across organizations. A model may then be used to determine trends or other relevant information (e.g., an optimal patient-dentist match determined by looking at utilization best provider outcomes, a dentist over-provision of certain services (as indicated by provider codes, thereby possibly indicative of fraud, etc.), thereby given the system the ability to determine if, when and how the organization can reduce expenses (e.g., by switching to other providers, etc.) or otherwise provide better care for its participating employees. The data models preferably evolve over time, continuously.

By applying machine learning to the patient-centric data, the system builds a comprehensive picture of the provider(s), their services, and patient interactions. Data models generated from the patient-centric data are then used to train machine learning models. The model(s) that are created are then used as a front-end to one or more of the other applications in the system. One such application provides selection of an optimal payment processor thereby providing more-efficient process settlement between a payer, and a provider.

Moreover, and according to another aspect, as patient profile(s) increase in size and complexity, the computing system itself is scaled dynamically to ensure that real-time processing is enabled. Thus, for example, one or more patient profiles may be processed in real-time against settlement, service eligibility or other system features using a single process on a single server or machine. As the size of a patient profile increases, the computing resources themselves preferably are intelligently-scaled. For example, in one embodiment, the system executes one server per profile running within a cluster of servers in a cloud environment. As needed, processing of a profile may be carried out over a cluster of servers operating within a multi-cluster cloud environment. Thus, as the patient profile increases with multi-dimensional data across different types of providers, services, and other information, the system allocates its computing resources dynamically and as-needed to maintain real-time data processing, claims processing, and reporting to the participating entities.

The foregoing has outlined some of the more pertinent features of the subject matter. These features should be construed to be merely illustrative. Many other beneficial results can be attained by applying the disclosed subject matter in a different manner or by modifying the subject matter as will be described.

BRIEF DESCRIPTION OF THE DRAWINGS

For a more complete understanding of the subject matter and the advantages thereof, reference is now made to the following descriptions taken in conjunction with the accompanying drawings, in which.

DETAILED DESCRIPTION

Figure 1:
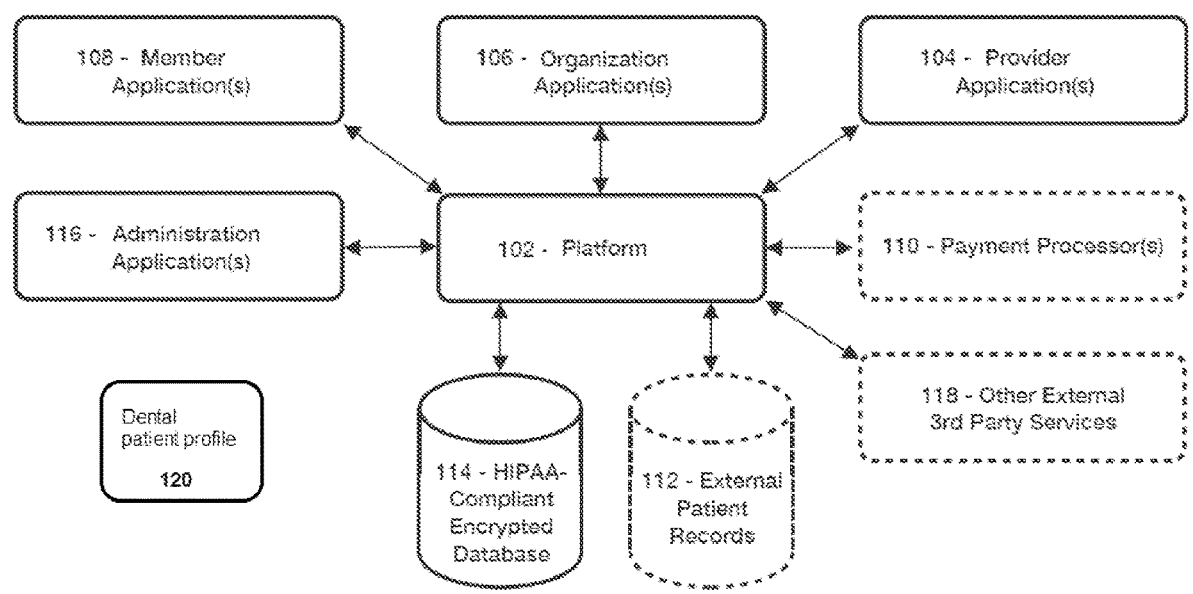
FIG. 1 is a block diagram depicting a benefits management system according to an aspect of this disclosure.

In one embodiment, and with reference to FIG. 1, a system 100 in which the techniques of this disclosure may be practiced comprises a collection of networked computers and devices. A computing platform 102 executes the basic data management functionality as will be described. Typically, the computing platform is managed and operated "as-a-service" by a service provider entity. The platform typically is accessible over the public Internet at a particular serviceprovider.com domain, or sub-domain. The platform 102 is securely-connected with a HIPAA-compliant infrastructure (typically via SSL/TLS connections), and that infrastructure includes data encrypted at rest, e.g., in an HIPAA-compliant encrypted database 114. The computing platform typically comprises a set of applications implemented as network-accessible services. One or more applications (services) may be combined with one another. An application (service) may be implemented using a set of computing resources that are co-located or themselves distributed. Typically, an application is implemented using one or more computing systems. The computing platform (or portions thereof) may be implemented in a dedicated environment, in an on-premises manner, as a cloud-based architecture, or some hybrid. As depicted, the computing platform 102 interoperates with one or more external payment processors 110 (e.g., credit card processors), and perhaps other external (third party) services 118. External patient records are typically supported in a database 112; these records may be accessed by the computing platform 102.

In one embodiment, and as depicted, the system 100 comprises several groups of client applications, namely, one or more provider applications 104, one or more organization applications 106, one or more member applications 108, and one or more administration applications 116. A member, typically an individual end user, uses a computing device (e.g., mobile phone, tablet, laptop or desktop computer, Internet-connected appliance, etc.) on which a member application 108 is executed. In a typical use case, the member application 108 is a mobile application (app) that a user obtains from a publicly-available source, such as a mobile application storefront. The provider, organization and administration applications 104, 106 and 116 typically execute on application servers in the computing system, and these applications are accessible via a browser or the like. Although typically these applications are network-accessible, e.g., via the publicly-routed Internet, the computing system may be implemented in a standalone or on-premises manner. In addition, one or more of the identified components may interoperate with some other enterprise computing system or application, e.g., a dental office portal. There may be one or more additional applications, such as a reimbursement application that handles out-of-network transactions against the below-described settlement algorithm.

One or more of the applications 104, 106 and 116 may be combined or integrated with one another.

Generalizing, the client applications and the platform (which acts as a server application to the clients) enable individuals and companies to self-insure a dental benefit tied to certain providers, and to facilitate associated payment transactions. In particular, these applications provide for the ability to transfer funds between and among payers and providers, the ability to create real-time billing estimates by reconciling past appointments, services rendered, and current Explanation of Benefits (EOB) usage, the ability to create dynamic and custom "plans" that enable custom benefits, the ability to create and manage dynamic and custom fee schedules that allow for customized service pricing, the ability to compare employee location with dentist locations and types to configure optimal plan suggestions for employers, the ability to obtain second opinions based on service estimation and patient records, and the like.

Preferably, the platform supports a machine learning component that automatically optimizes plan configuration for employers based on aggregate employee network and benefits usage and information.

Preferably, the platform also supports a machine learning component that constructs a HIPAA-compliant patient profile for each member. This profile enables the applications and platform to become personalized to each member. Generalizing, the HIPAA-compliant patient profile (for each member) is instantiated as a particular data structure, which in the context of a dental benefit is sometimes referred to herein as a dental patient profile 120. Unlike traditional service records that are simply static and just include a service treatment history, the patient profile is a data construct that evolves in a multi-dimensional manner, typically via machine learning. The data structure supports (or can reference) all of the information normally found in traditional service records (such as in database 112), but it is also structured to include n-dimensions of additional data, including without limitation: benefits history, location information, provider history, employment history, personally-identifiable information, and more information, preferably according to an extensible data model. By applying machine learning, the system builds a comprehensive picture of the patient (or a patient group), and the profile is used to more-efficiently process settlement between a payer, and a provider.

As described above, as patient profile(s) increase in size and complexity, the computing system 102 itself is scaled dynamically to ensure that real-time processing is enabled. Thus, for example, one or more patient profiles may be processed in real-time against settlement, service eligibility or other system features using a single process on a single server or machine. As the size of a patient profile increases, the computing resources themselves preferably are intelligently-scaled. For example, in one embodiment, the system executes one server per profile running within a cluster of servers in a cloud environment. As needed, processing of a profile may be carried out over a cluster of servers operating within a multi-cluster cloud environment. Thus, as the patient profile increases with multi-dimensional data across different types of providers, services, and other information, the system allocates its computing resources dynamically and as-needed to maintain real-time data processing, claims processing, and reporting to the participating entities.

Thus, the computing platform 200 creates and maintains a patient-centric profile 202 for each member. The patient profile 202 is instantiated as a flexible and extensible data structure that typically evolves as the member continues to interact with the platform. Thus, for example, the member may register with the platform to use a single provider, but over time the member's requirements may change, with the user then establishing relationships with additional providers, different organizations (employers), different payment providers, and so forth. Preferably, and as noted above, the platform applies one or more machine learning algorithms 208 to the individual member profile(s), as they evolve in size and complexity. The machine learning (ML) algorithm(s) generate one or more data models 205, as previously described. As the individual profiles evolve, processing on a member's dental visit/reimbursement may then require more complex interactions with the various application(s) that comprise the system.

As also depicted, preferably the computing platform 200 includes a resource allocation mechanism 204 that dynamically determines the appropriate computing resource(s) 206 (e.g., machines, processors, processes, etc.) to allocated to a particular member as the system is tasked to handle a particular settlement or other operation. Depending on the patient profile, the resource allocation mechanism 204 allocates the necessary underlying computing resources (e.g., physical or virtual machines or clusters, memory, storage, servers, etc.) 206 to process the settlement accordingly. The resource allocation mechanism 204 also preferably leverages the machine learning component 208, e.g., to learn a "best" allocation of underlying computing resources for a particular member, and saves that processing state (e.g., in the profile itself, or in a separate cache or data store). In this manner, the computing resources necessary to process a settlement may are allocated, used to process the settlement, and then returned for use to process settlement(s) for other members.

Typically, one or more members are processed by a single server executing on a single physical or virtual machine. As the size and/or complexity of a given profile increases, however, the server may then be dedicated to processing just the given profile. As the profile becomes still larger, an additional server may then be allocated by the resource allocation mechanism, and so on as necessary.

The resource allocation mechanism preferably operates as a multi-threaded control mechanism that continually receives information about the state and status of the various computing resources, allocates processing threads/instances to individual member settlement(s), manages the resources as they are used to process the settlement(s), and returns (frees) the computing resources back to the underlying system when a particular settlement is completed. The resource allocation mechanism may comprise a component of a cloud computing infrastructure that is leveraged for this purpose.

The nature and type of Machine Learning (ML) algorithms that are used to process the patient-centric data (from the patient profiles) into one or more data models may vary. ML algorithms iteratively learn from the patient-centric data, thus allowing the system to find hidden insights without being explicitly programmed where to look. ML tasks are typically classified into various categories depending on the nature of the learning signal or feedback available to a learning system, namely supervised learning, unsupervised learning, and reinforcement learning. In supervised learning, the algorithm trains on labeled historic data and learns general rules that map input to output/target. The discovery of relationships between the input variables and the label/target variable in supervised learning is done with a training set, and the system learns from the training data. In this approach, a test set is used to evaluate whether the discovered relationships hold and the strength and utility of the predictive relationship is assessed by feeding the model with the input variables of the test data and comparing the label predicted by the model with the actual label of the data. The most widely used supervised learning algorithms are Support Vector Machines, Linear Regression, Logistic Regression, Naive Bayes, and Neural Networks.

In unsupervised machine learning, the algorithm trains on unlabeled data. The goal of these algorithms is to explore the data and find some structure within. The most widely used unsupervised learning algorithms are Cluster Analysis and Market Basket Analysis. In reinforcement learning, the algorithm learns through a feedback system. The algorithm takes actions and receives feedback about the appropriateness of its actions and based on the feedback, modifies the strategy and takes further actions that would maximize the expected reward over a given amount of time.

The following provides additional details regarding supervised machine learning, which is the preferred technique used in the patient-centric data approach herein. As noted above, supervised learning is the machine learning task of inferring a function from labeled training data. The training data consist of a set of training examples. In supervised learning, typically each example is a pair consisting of an input object (typically a vector), and a desired output value (also called the supervisory signal). A supervised learning algorithm analyzes the training data and produces an inferred function, which can be used for mapping new examples. An optimal scenario allows for the algorithm to correctly determine the class labels for unseen instances. This requires the learning algorithm to generalize reasonably from the training data to unseen situations.

For supervised learning, the following steps are used. An initial determination is what kind of data is to be used as a training set. The training set is then gathered. In particular, a set of input objects is gathered and corresponding outputs are also gathered, either from human experts or from measurements. Then, an input feature representation of the learned function is determined. In this approach, typically the input object is transformed into a feature vector, which contains a number of features that are descriptive of the object. The structure of the learned function and corresponding learning algorithm are then determined. For example, support vector machines or decision trees may be used. The learning algorithm is then run on the gathered training set.

Some supervised learning algorithms require a user to determine certain control parameters. These parameters may be adjusted by optimizing performance on a subset (called a validation set) of the training set, or via cross-validation. The accuracy of the learned function is then evaluated. After parameter adjustment and learning, the performance of the resulting function is measured on a test set that is separate from the training set.

The patient-centric profiles constantly evolve in size and complexity. Meanwhile, as the system scales (i.e., as the number of members, organizations, providers, etc. increases), the data models themselves become more complex. Nevertheless, the infrastructure maintains its ability to process the settlement(s) in real-time and, in particular, by adjusting (via the resource allocation mechanism) the necessary underlying computing resources. The computing platform may also include a scheduling mechanism that in turn manages one or more the resource allocation mechanisms to ensure that the system operates efficiently and in a highly-available, highly-scalable, and efficient manner.

As used herein, and as depicted in FIG. 1, various "entities" access and use the computing platform 102, which is preferably cloud-based. These entities include, for example, members, providers, payers and administrators. As used herein, members are entities that access the system via member applications 108 tied to the platform. Through these mobile apps, members enroll, view benefits, and manage treatment. Members typically are primary or family members. A family member can utilize a primary member's payment method.

Providers access the system typically via one or more applications 104 tied to the platform. Through these web applications, providers can determine member eligibility, view past treatment, schedule new treatments, send fee estimates, and collect payment for services rendered.

Payers can be at a member level or at an organization level (collection of members), such as an employer. Payers access the system via organization application 106 and add payment methods, typically in one of two ways. For payers that are members who wish to pay via the platform for total costs or for out-of-pocket costs not covered by the organization providing the benefit, they directly add payment methods during enrollment or from their account in the mobile app. For payers that are organizations, they access and adjust their payment and benefit through a web application tied to the platform.

In this approach herein, preferably payment is automatically transferred via the system from one or more payers to a single provider once the provider submits an invoice for payment. Payment transaction processing preferably leverages existing payment solutions 110 (e.g., Braintree, Stripe, or the like), or a more custom solution may be implemented.

In an employer pay payment flow, a member typically is associated with an employer. In one embodiment, the employer pays a per month per live covered fee to the system to use the service. Services rendered by a provider are paid directly from an employer's ACH account.

In a self-pay payment flow, a member can become a primary member by adding his or her family members (e.g., spouses, dependents, etc.). The family pay payment flow typically allows the family member to automatically use the primary member's payment method, whether the primary member is using employer pay, or self-pay.

In a family pay payment flow, a member can become a primary member by adding his or her family members (spouses and dependents). The family pay payment flow allows the family member to automatically use the primary member's payment method whether the primary member is using employer pay or self-pay.

The computing platform enables organizations and individuals to get access to affordable dental care without the need to contract with any insurance company. The platform enables participants to obtain high quality, affordable, and easy to understand dental benefits. Thus, for example, using the member application members can find their dentist, manage appointments, understand costs, pay negotiated rates, and manage his or her entire family. Dentists (providers) use the provider application to understand member benefits and get paid faster. Typically, dentists get paid directly through the platform. Organizations (payers) of any size are able to build pay-as-you-go dental plans that fit their budgets. Unused benefit dollars stay in the organization's bank account, and members will always have a clear, real-time picture of their benefits.

In an example use case, an organization self-insures its participating employees in the following manner. The organization sets up its employer plan using the organization application 106 (an employer portal). In particular, the employer portal enables the organization to manage enrollment, employee status, COBRA, and other such information. The organization application preferably integrates with existing payroll, benefit, and HCM systems. It is presumed that providers (dentists, dental offices, other providers of related services) have enrolled with the platform using the provider application(s) 104. The organization informs its employees to obtain the member application(s) 108, e.g., via an app store. Employees download the app, register, and add a payment method. Once the plan is setup, the company contributes its usual monthly premiums into a company-owned bank account. No funds are transferred, however, until services are rendered, and payments are handled seamlessly and efficiently, all without involvement of any insurance company. For the providers, if the patient has an employer plan, the platform (service provider) moves the money on behalf of the employer, directly from their bank account to the dental office. If the patient only has an individual plan (i.e., he or she is not affiliated with an organization), the platform charges the patient's credit card on file, once again moves the money directly to the dentist office's bank account. The dentist office does not make any claim submission. The Bento Dentist Portal will tell you in real-time the amount covered by the plan, and the patient portion (if applicable), on a per service basis. You'll get paid directly after services are complete.

Preferably, a participating organization can interact with the platform to see its member's data (in an aggregating manner, compliant with HIPAA), view the resulting data model(s), run "what-if" scenario(s) against these data models, receive reports and other analytics and insights, and so forth.

Preferably, the computing platform also includes tooling (automation) 210 by which information provided from evaluating a patient-centric data model is then used to automatically adjust underlying computing resources that are used by the system, e.g., a selected payment processor, a protocol for interacting with a processor, a frequency of interaction, or the like. This automatic adjustment of computing resources may also adjust the nature and type of the underlying computing resources that are used to process a particular member (or organization's members, etc.), thereby enabling dynamic adjustment of such resources based on the data model(s) or the underlying patient profile data that generates these models. This integrates the benefits processing as described below into a practical application, and it provides for an improved (more computationally- and storage-efficient) operation of the distributed computing platform even as the patient-centric profile(s) evolve and the number of participants increases.

Figure 2:
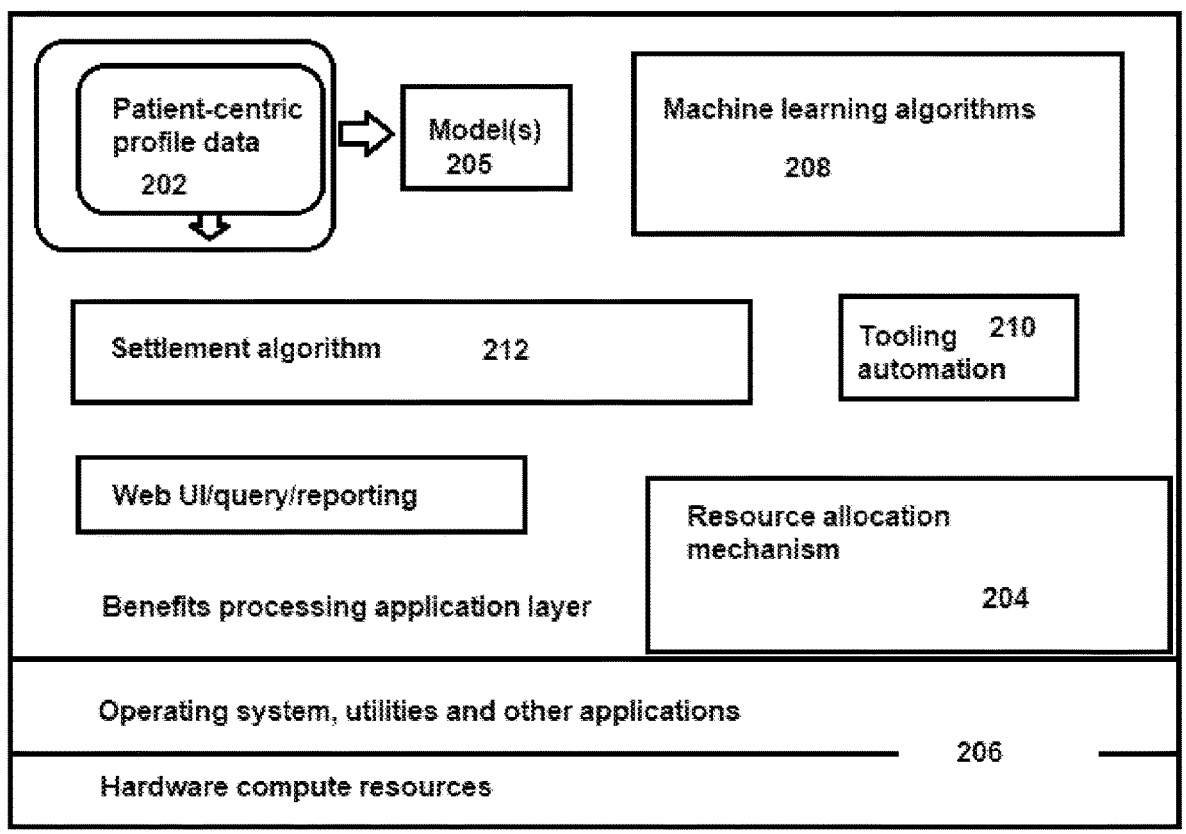
FIG. 2 is a block diagram depicting further details of the system in one embodiment.

Preferably, the platform supports execution of a settlement algorithm (FIG. 2, 212) that leverages a combination of patient service/appointment data and benefit coverage to give a user a real-time cost assessment (e.g., "plan pays versus you pay"). Typically, there is an instance of this algorithm that is executed by the platform for each appointment, at time of creation, and at time of payment. In addition, an instance of this algorithm is executed by the platform when an estimate of treatment cost is requested by a provider. The following sets forth a preferred implementation of this algorithm.

Settlement algorithm

```
# Six possible paths for settlement:
# 1. Self-Pay
# 1. Employer Custom Plan
# 2. Employer Standard Plan (matches with one of doctor's supported plans)
# 3. Employer Standard Plan (member plan is lower than doctor's lowest plan)
# 4. Employer Standard Plan (member plan is higher than doctor's highest plan)
# 5. Employer Standard Plan (member plan is in between doctor's plans)
# NOTE: Two new Plan concepts are used, namely:

# 1) Plan Collection
# Plan Collection ties multiple plans together
# (e.g. Plan Collection = Region 1 - North East)

# 2) Plan Rank
# Plan Rank allows us to indicate higher/lower plans
# (e.g. Plan Rank = 3)
MaximumConvenienceFee = 60   # This should be a variable amount (60 to start)
PercentConvenienceFee = 0.2  # This should be a variable amount (20% to start)
TotalCost = 0
PlanPays = 0
YouPay = 0
ConvenienceFee = 0
If Member IS using Self Pay
    if Member Plan MATCHES a Doctor's Supported Plan
        Plan Pay Amount comes from Member Plan EOB & Fee Schedule for Region
        Service Cost comes Doctor Plan Fee Schedule for Region
    else if Member Plan Rank IS LOWER than Doctor's Lowest Plan Rank
        # e.g. Member = Silver (Rank 3), Doctor = Gold (Rank 2), Platinum (Rank 1)
        Plan Pay Amount comes from Member Plan EOB & Fee Schedule for Region     # e.g. Silver
        Service Cost comes from Doctor's Lowest Plan Fee Schedule for Region     # e.g. Gold
    else if Member Plan Rank IS HIGHER than Doctor's Highest Plan Rank
        # e.g. Member = Platinum (Rank 1), Doctor = Silver (Rank 3), Gold (Rank 2)
        Plan Pay Amount comes from Member Plan EOB & Fee Schedule for Region     # e.g. Platinum
        Service Cost comes from Doctor's Highest Plan Fee Schedule for Region    # e.g. Gold
    else
        # e.g. Member = Gold (Rank 2), Doctor = Silver (Rank 3), Platinum (Rank 1)
        Plan Pay Amount comes from Member Plan EOB & Fee Schedule for Region     # e.g. Platinum
        Service Cost comes from Doctor's Lowest Plan Fee Schedule for Region     # e.g. Silver
    For each Service in Appointment:
        YouPayForService = 0
        If Service IS Finished:
            YouPayForService = Service Cost
        YouPay = YouPay + YouPayForService
    if Member.ConvenienceFeeToDate < MaximumConvenienceFee:
        ConvenienceFeeLeft = MaximumConvenienceFee - Member.ConvenienceFeeToDate
        ConvenienceFee = YouPay * PercentConvenienceFee
        if (ConvenienceFee > ConvenienceFeeLeft):
            ConvenienceFee = ConvenienceFeeLeft
        Member.ConvenienceFeeToDate = Member.ConvenienceFeeToDate - ConvenienceFee
Else Member IS using Employer Payment
    Check if member has a custom plan
    If Member HAS a custom plan:
        if Custom Plan Network MATCHES a Doctor's Supported Plan
            Plan Pay Amount comes from Custom Plan Network EOB & Fee Schedule for Region
            Service Cost comes Doctor Plan Fee Schedule for Region
        else if Custom Plan Network Rank IS LOWER than Doctor's Lowest Plan Rank
            # e.g. Member = Silver (Rank 3), Doctor = Gold (Rank 2), Platinum (Rank 1)
            Plan Pay Amount comes from Custom Plan Network EOB & Fee Schedule for Region  # e.g. Silver
            Service Cost comes from Doctor's Lowest Plan Fee Schedule for Region          # e.g. Gold
        else if v Rank IS HIGHER than Doctor's Highest Plan Rank
            # e.g. Member = Platinum (Rank 1), Doctor = Silver (Rank 3), Gold (Rank 2)
            Plan Pay Amount comes from Custom Plan Network EOB & Fee Schedule for Region
```

| Settlement algorithm |
|---|

```
        # e.g. Platinum
                Service Cost comes from Doctor's Highest Plan Fee Schedule for Region       # e.g. Gold
            else
                # e.g. Member = Gold (Rank 2), Doctor = Silver (Rank 3), Platinum (Rank 1)
                Plan Pay Amount comes from Custom Plan Network EOB & Fee Schedule for Region
        # e.g. Platinum
                Service Cost comes from Doctor's Lowest Plan Fee Schedule for Region
        # e.g. Silver
            For each Service in Appointment:
                PlanPaysForService = 0
                YouPayForService = 0
                If Service IS Finished:
                    If Service IS Covered by Custom Plan AND
                    If Member has NOT reached a Service Limit:
                        PlanPaysForService = Custom Plan Network Fee Schedule Service Cost
                        YouPayForService = Doctor's Service Cost − PlanPaysForService
                    Else: # Out of Pocket
                        YouPayForService = Doctor's Service Cost
                    # Adjust amount for benefit Remaining
                    if Service IS Standard
                        if Additional Fixed Amount Remaining < YouPayForService:
                            PlanPaysForService = PlanPaysForService + Member Benefit Remaining
                            Member Benefit Remaining = 0
                            YouPayForService = Doctor Service Cost − PlanPaysForService
                        else # Additional Fixed Amount Remaining >= YouPayForService
                            Member Benefit Remaining = Member Benefit Remaining − YouPayForService
                            PlanPaysForService = PlanPaysForService + YouPayForService
                            YouPayForService = 0
                    else Service IS Orthodontic (ADACODE is 8000-8999)
                        if Ortho Benefit Remaining < YouPayForService:
                            PlanPaysForService = PlanPaysForService + Ortho Benefit Remaining
                            Ortho Benefit Remaining = 0
                            YouPayForService = Doctor Service Cost − PlanPaysForService
                        else # Ortho benefit Remaining >= YouPayForService
                            Ortho Benefit Remaining = Ortho Benefit Remaining − YouPayForService
                            PlanPaysForService = PlanPaysForService + YouPayForService
                            YouPayForService = 0
                PlanPays = PlanPays + PlanPaysForService
                YouPay = YouPay + YouPayForService
    Else Member DOES NOT have a custom plan:
        # Determine how costs are calculated based on Member Plan vs. Doctor Plan
        # NOTE: Plan pay ALWAYS comes from Member EOB and Member Fee Schedule in Plan
        # NOTE: Total Cost ALWAYS comes from the appropriate selected Doctor's Fee Schedule
        if Member Plan MATCHES a Doctor's Supported Plan
            Plan Pay Amount comes from Member Plan EOB & Fee Schedule for Region
            Service Cost comes Doctor Plan Fee Schedule for Region
        else if Member Plan Rank IS LOWER than Doctor's Lowest Plan Rank
            # e.g. Member = Silver (Rank 3), Doctor = Gold (Rank 2), Platinum (Rank 1)
            Plan Pay Amount comes from Member Plan EOB & Fee Schedule for Region
        # e.g. Silver
            Service Cost comes from Doctor's Lowest Plan Fee Schedule for Region
        # e.g. Gold
        else if Member Plan Rank IS HIGHER than Doctor's Highest Plan Rank
            # e.g. Member = Platinum (Rank 1), Doctor = Silver (Rank 3), Gold (Rank 2)
            Plan Pay Amount comes from Member Plan EOB & Fee Schedule for Region
        # e.g. Platinum
            Service Cost comes from Doctor's Highest Plan Fee Schedule for Region
        # e.g. Gold
            else
                # e.g. Member = Gold (Rank 2), Doctor = Silver (Rank 3), Platinum (Rank 1)
                Plan Pay Amount comes from Member Plan EOB & Fee Schedule for Region
```

| Settlement algorithm |
| --- |
| ```
            # e.g. Platinum
                    Service Cost comes from Doctor's Lowest Plan Fee Schedule for Region        # e.g.
Silver
            # Once we know where Plan Pays / Fee Schedule comes from
            For each Service in Appointment:
                    PlanPaysForService = 0
                    YouPayForService = 0
                    # Find out if Member is Covered, What Percent is covered by EOB, If any limits are
exceeded, deductible eligible
                    Check Member Service Coverage for Service ADACode( )
                        Check if Service is covered by EOB
                        Check what percentage is covered by EOB
                        Check if any limits have been exceeded for the Service
                        Check if the service is deductible eligible from the EOB (typically SRS and
MRS services)
                    if Service is Finished AND
                    if Member EOB Percent Coverage from Service Coverage is > 0 AND
                    if Service has not exceeded Member EOB limits (teeth, quadrant, etc) AND
                    if Member has Benefit Remaining > 0:
                        PlanPaysForService = Member Plan Service Cost * EOB Percent Coverage
                        if Service is Deductible eligible AND
                        if Member Deductible IS NOT met:
                            PlanPaysForService = (Member Plan Service Cost − Deductible
Amount) * EOB Percent Coverage
                            Set Member Deductible met to be TRUE
                        YouPayForService = Doctor Service Cost − PlanPaysForService
                        # Adjust amount for benefit Remaining
                        if Service IS Standard:
                            if Member Benefit Remaining < PlanPaysForService:
                                PlanPaysForService = Member Benefit Remaining
                                Member Benefit Remaining = 0
                                YouPayForService = Doctor Service Cost −
PlanPaysForService
                            else # Member Benefit Remaining >= PlanPaysForService
                                Member Benefit Remaining = Member Benefit Remaining −
PlanPaysForService
                        else Service IS Orthodontic (ADACODE is 8000-8999):
                            if Ortho Benefit Remaining < PlanPaysForService:
                                PlanPaysForService = Ortho Benefit Remaining
                                Ortho Benefit Remaining = 0
                                YouPayForService = Doctor Service Cost −
PlanPaysForService
                            else # Ortho Benefit Remaining >= PlanPaysForService
                                Ortho Benefit Remaining = Ortho Benefit Remaining −
PlanPaysForService
                    else: # Completely out of pocket expense
                        YouPayForService = Doctor Service Cost
                    PlanPays = PlanPays + PlanPaysForService
                    YouPay = YouPay + YouPayForService
TotalCost = PlanPays + YouPay + ConvenienceFee
``` |

According to another aspect, preferably the system automatically matches a member against available enrollments from organizations using a unique identifier (e.g. SSN). This makes it easy for the system to facilitate the enrollment into benefits. In use, preferably an individual's SSN is verified (using a third party identity service) as a member, over a secure communication channel, after which the individual is then a member. Once enrolled, the system exposes to the member (after the member has executed a secure login to the system), all available benefits that have been associated with the member's particular SSN.

Enabling Technologies

One or more functions of the computing platform of this disclosure may be implemented in a cloud-based architecture. As is well-known, cloud computing is a model of service delivery for enabling on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. Available services models that may be leveraged in whole or in part include: Software as a Service (SaaS) (the provider's applications running on cloud infrastructure); Platform as a service (PaaS) (the customer deploys applications that may be created using provider tools onto the cloud infrastructure); Infrastructure as a Service (IaaS) (customer provisions its own processing, storage, networks and other computing resources and can deploy and run operating systems and applications).

The platform may comprise co-located hardware and software resources, or resources that are physically, logically, virtually and/or geographically distinct. Communication networks used to communicate to and from the platform services may be packet-based, non-packet based, and secure or non-secure, or some combination thereof.

More generally, the techniques described herein are provided using a set of one or more computing-related entities (systems, machines, processes, programs, libraries, functions, or the like) that together facilitate or provide the described functionality described above. In a typical implementation, a representative machine on which the software executes comprises commodity hardware, an operating system, an application runtime environment, and a set of applications or processes and associated data, that provide the functionality of a given system or subsystem. As described, the functionality may be implemented in a stand-alone machine, or across a distributed set of machines.

Enabling technologies for the machine learning algorithm include, without limitation, vector autoregressive modeling (e.g., Autoregressive Integrated Moving Average (ARIMA)), state space modeling (e.g., using a Kalman filter), a Hidden Markov Model (HMM), recurrent neural network (RNN) modeling, RNN with long short-term memory (LS™), Random Forests, Generalized Linear Models, Extreme Gradient Boosting, Extreme Random Trees, and others. By applying these modeling techniques, new types of features are extracted, e.g., as follows: model parameters (e.g. coefficients for dynamics, noise variance, etc.), latent states, and predicted values for a next couple of observation periods.

Typically, but without limitation, a client device is a mobile device, such as a smartphone, tablet, or wearable computing device. Such a device comprises a CPU (central processing unit), computer memory, such as RAM, and a drive. The device software includes an operating system (e.g., Google® Android™, or the like), and generic support applications and utilities. The device may also include a graphics processing unit (GPU). The mobile device also includes a touch-sensing device or interface configured to receive input from a user's touch and to send this information to processor. The touch-sensing device typically is a touch screen. The mobile device comprises suitable programming to facilitate gesture-based control, in a manner that is known in the art.

Generalizing, the mobile device is any wireless client device, e.g., a cellphone, pager, a personal digital assistant (PDA, e.g., with GPRS NIC), a mobile computer with a smartphone client, or the like. Other mobile devices in which the technique may be practiced include any access protocol-enabled device (e.g., an Android™-based device, or the like) that is capable of sending and receiving data in a wireless manner using a wireless protocol. Typical wireless protocols are: WiFi, GSM/GPRS, CDMA or WiMax. These protocols implement the ISO/OSI Physical and Data Link layers (Layers 1 & 2) upon which a traditional networking stack is built, complete with IP, TCP, SSL/TLS and HTTP.

In a representative embodiment, the mobile device is a cellular telephone that operates over GPRS (General Packet Radio Service), which is a data technology for GSM networks. In addition to a conventional voice communication, a given mobile device can communicate with another such device via many different types of message transfer techniques, including SMS (short message service), enhanced SMS (EMS), multi-media message (MMS), email, WAP, paging, or other known or later-developed wireless data formats. Generalizing, a mobile device as used herein is a 3G—(or next generation) compliant device that includes a subscriber identity module (SIM), which is a smart card that carries subscriber-specific information, mobile equipment (e.g., radio and associated signal processing devices), a man-machine interface (MMI), and one or more interfaces to external devices (e.g., computers, PDAs, and the like). The techniques disclosed herein are not limited for use with a mobile device that uses a particular access protocol. The mobile device typically also has support for wireless local area network (WLAN) technologies, such as Wi-Fi. WLAN is based on IEEE 802.11 standards.

The underlying network transport may be any communication medium including, without limitation, cellular, wireless, Wi-Fi, small cell (e.g., femto), and combinations thereof.

Each above-described process preferably is implemented in computer software as a set of program instructions executable in one or more processors, as a special-purpose machine.

Representative machines on which the subject matter herein is provided may be Intel Pentium-based computers running a Linux or Linux-variant operating system and one or more applications to carry out the described functionality. One or more of the processes described above are implemented as computer programs, namely, as a set of computer instructions, for performing the functionality described.

While the above describes a particular order of operations performed by certain embodiments of the invention, it should be understood that such order is exemplary, as alternative embodiments may perform the operations in a different order, combine certain operations, overlap certain operations, or the like. References in the specification to a given embodiment indicate that the embodiment described may include a particular feature, structure, or characteristic, but every embodiment may not necessarily include the particular feature, structure, or characteristic.

While the disclosed subject matter has been described in the context of a method or process, the subject matter also relates to apparatus for performing the operations herein. This apparatus may be a particular machine that is specially constructed for the required purposes, or it may comprise a computer otherwise selectively activated or reconfigured by a computer program stored in the computer. Such a computer program may be stored in a computer readable storage medium, such as, but is not limited to, any type of disk including an optical disk, a CD-ROM, and a magnetic-optical disk, a read-only memory (ROM), a random access memory (RAM), a magnetic or optical card, or any type of media suitable for storing electronic instructions, and each coupled to a computer system bus.

A given implementation of the computing platform is software that executes on a hardware platform running an operating system such as Linux. A machine implementing the techniques herein comprises a hardware processor, and non-transitory computer memory holding computer program instructions that are executed by the processor to perform the above-described methods.

The functionality may be implemented with other application layer protocols besides HTTP/HTTPS, or any other protocol having similar operating characteristics.

There is no limitation on the type of computing entity that may implement the client-side or server-side of the connection. Any computing entity (system, machine, device, program, process, utility, or the like) may act as the client or the server.

While given components of the system have been described separately, one of ordinary skill will appreciate that some of the functions may be combined or shared in given instructions, program sequences, code portions, and the like. Any application or functionality described herein may be implemented as native code, by providing hooks into another application, by facilitating use of the mechanism as a plug-in, by linking to the mechanism, and the like.

The platform functionality may be co-located or various parts/components may be separately and run as distinct functions, perhaps in one or more locations (over a distributed network).

Each above-described process preferably is implemented in computer software as a set of program instructions executable in one or more processors, as a special-purpose machine.

The techniques herein generally provide for the above-described improvements to a technology or technical field, as well as the specific technological improvements to various fields including distributed benefits management, all as described above.

What is claimed is as follows:

1. A method of benefit processing, comprising:
configuring a computing platform to provide a benefit-as-a-service;
receiving, from each of one or more service providers, a first data set, the first data set including data associated with the service provider;
receiving, from each of a set of users, a second data set, the second data set including data associated with each of the users, the set of users being associated with an entity;
for each user, building and maintaining an n-dimensional patient profile, wherein information in an n-dimensional patient profile varies dynamically based on the user's interactions with one or more service providers, and wherein size and complexity of the n-dimensional patient profile change continuously as the user's interactions with or more service providers occur over a time period;
allocating computing resources dynamically for executing a settlement algorithm based at least in part on the size and complexity of the n-dimensional patient profiles for the set of users; and
responsive to receipt of a third data set, the third data set comprising information identifying a requested service, an appointment date, and a benefit coverage for an applicable entity plan, executing the settlement algorithm on the dynamically-allocated computing resources and returning a cost assessment;
wherein allocating computing resources and executing the settlement algorithm includes, for at least one given user and the associated n-dimensional patient profile of the given user, receiving information about a state of the computing resources, based on the size and complexity of the n-dimensional patient profile of the given user, allocating a subset of the computing resources to process the n-dimensional patient profile of the given user in association with the third data set and, thereafter, returning the allocated subset of the computing resources back to the computing platform for use to process settlements for other users.

2. The method as described in claim 1, further including applying machine learning to information derived from the n-dimensional patient profiles for the set of users to generate one or more data models, wherein at least one data model is a patient-provider data model.

3. The method as described in claim 1, wherein, for at one least one user of the set of users, an optimal allocation of computing resources based on the n-dimensional patient profile for that user is learned and saved into the n-dimensional patient profile for that user.

4. The method as described in claim 1, wherein the cost assessment is provided without interaction with a third party insurance provider.

5. The method as described in claim 1, wherein the benefit is a dental benefit.

6. The method as described in claim 1, wherein the subset of the computing resources includes a set of processing instances or threads.

7. The method as described in claim 2, wherein the subset of the computing resources are selected based on applying the patient-provider data model associated with the given user.

* * * * *